US012642909B2

(12) United States Patent (10) Patent No.: US 12,642,909 B2
Yang (45) Date of Patent: Jun. 2, 2026

(54) PATCH-TYPE DRUG INFUSION DEVICE

(71) Applicant: MEDTRUM TECHNOLOGIES INC., Shanghai (CN)

(72) Inventor: Cuijun Yang, Shanghai (CN)

(73) Assignee: MEDTRUM TECHNOLOGIES INC., Shanghai (CN)

( * ) Notice: Subject to any disclaimer, the term of this patent is extended or adjusted under 35 U.S.C. 154(b) by 607 days.

(21) Appl. No.: 18/033,359

(22) PCT Filed: Jan. 5, 2021

(86) PCT No.: PCT/CN2021/070209
§ 371 (c)(1),
(2) Date: Apr. 24, 2023

(87) PCT Pub. No.: WO2022/088500
PCT Pub. Date: May 5, 2022

(65) Prior Publication Data
US 2023/0398287 A1 Dec. 14, 2023

(30) Foreign Application Priority Data
Oct. 30, 2020 (WO) ................ PCT/CN2020/125031

(51) Int. Cl.
*A61M 5/158* (2006.01)
*A61M 5/36* (2006.01)
(Continued)

(52) U.S. Cl.
CPC .............. *A61M 5/158* (2013.01); *A61M 5/36* (2013.01); *A61M 2005/1402* (2013.01);
(Continued)

(58) Field of Classification Search
CPC .... A61M 5/158; A61M 5/36; A61M 5/14244; A61M 5/14248; A61M 2005/1402; A61M 2005/14252
(Continued)

(56) References Cited

U.S. PATENT DOCUMENTS

| | | | |
|---|---|---|---|
| 10,279,106 B1 | 5/2019 | Cook et al. | |
| 2008/0294094 A1* | 11/2008 | Mhatre | A61M 5/14248 604/65 |
| 2016/0158436 A1* | 6/2016 | Yang | F04B 53/144 604/113 |

FOREIGN PATENT DOCUMENTS

| | | |
|---|---|---|
| CN | 1556716 | 12/2004 |
| CN | 103228303 | 7/2013 |

(Continued)

OTHER PUBLICATIONS

"International Search Report (Form PCT/ISA/210) of PCT/CN2021/070209," mailed on Jul. 29, 2021, pp. 1-2.

*Primary Examiner* — Phillip A Gray
(74) *Attorney, Agent, or Firm* — JCIP GLOBAL INC.

(57) ABSTRACT
A patch-type drug infusion device includes a control structure provided with multiple first fastening portions and first electrical contacts; and an infusion structure including a case, a power supply, a flexible circuit board, and an elastic conductor, and provided with multiple second electrical contacts and second fastening portions that cooperate with the first fastening portions. The first fastening portions and the second fastening portions are fastened, the first electrical contacts connect with the corresponding second electrical contacts, making the structure more compact and improving the space utilization rate inside the infusion structure.

10 Claims, 3 Drawing Sheets

(51) Int. Cl.

| | | |
|---|---|---|
| *A61M 5/14* | (2006.01) | |
| *A61M 5/142* | (2006.01) | |
| *A61M 5/162* | (2006.01) | |

(52) U.S. Cl.
CPC ..... *A61M 5/14244* (2013.01); *A61M 5/14248* (2013.01); *A61M 2005/14252* (2013.01); *A61M 2005/1581* (2013.01); *A61M 2005/1585* (2013.01); *A61M 2005/1623* (2013.01)

(58) Field of Classification Search
USPC ......................................................... 604/67
See application file for complete search history.

(56) References Cited

FOREIGN PATENT DOCUMENTS

| | | |
|---|---|---|
| CN | 104784777 | 7/2015 |
| CN | 107158512 | 9/2017 |
| CN | 111544703 | 8/2020 |
| KR | 20140101255 | 8/2014 |

* cited by examiner

PATCH-TYPE DRUG INFUSION DEVICE

CROSS-REFERENCE TO RELATED APPLICATION

This application is a 371 of international application of PCT application serial no. PCT/CN2021/070209, filed on Jan. 5, 2021, which claims the priority benefit of PCT application no. PCT/CN2020/125031, filed on Oct. 30, 2020. The entirety of each of the above-mentioned patent applications is hereby incorporated by reference herein and made a part of this specification.

TECHNICAL FIELD

The present invention mainly relates to the field of medical instruments, in particular to a patch-type drug infusion device.

BACKGROUND

The pancreas in a normal person can automatically monitor the amount of glucose in the blood and automatically secrete the required dosage of insulin/glucagon. However, for diabetic patients, the function of the pancreas is abnormal, and the pancreas cannot normally secrete required dosage of insulin. Therefore, diabetes is a metabolic disease caused by abnormal pancreatic function and also a lifelong disease. At present, medical technology cannot cure diabetes, but can only control the onset and development of diabetes and its complications by stabilizing blood glucose.

Patients with diabetes need to check their blood glucose before injecting insulin into the body. At present, most of the detection methods can continuously detect blood glucose, and send the blood glucose data to the remote device in real time for the user to view. This detection method is called Continuous Glucose Monitoring (CGM), which requires the detection device to be attached to the surface of the patients' skin, and the sensor carried by the device is inserted into the subcutaneous tissue fluid for testing. According to the blood glucose (BG) level, the infusion device, as a closed-loop or semi-closed-loop artificial pancreas, injects the currently required insulin dose.

However, the internal space utilization rate of the infusion component of the current drug infusion device is low, and the structure is not compact, resulting in larger volume of the infusion device.

Therefore, in the prior art, there is an urgent need for a drug infusion device that improves the utilization of the internal space of the infusion device.

BRIEF SUMMARY OF THE INVENTION

The invention discloses a patch-type drug infusion device which is provided with a flexible circuit board with strong plasticity. According to the structural characteristics, the internal space of the infusion structure can be fully utilized, making the structure more compact and improving the space utilization rate inside the infusion structure.

The invention discloses a patch-type drug infusion device, which comprises: a control structure provided with multiple first fastening portions and first electrical contacts exposed on the surface of the control structure; and an infusion structure including a case, a power supply, a flexible circuit board, and an elastic conductor one end of which is electrically connected to the electrical connection end on the flexible circuit board while the other end is electrically connected to the power supply, and provided with multiple second electrical contacts exposed on the surface of the case and second fastening portions that cooperate with the first fastening portions, the first fastening portions and the second fastening portions are fastened, the first electrical contacts connect with the corresponding second electrical contacts.

According to one aspect of the present invention, the first fastening portions and the second fastening portions include one or more of hooks, blocks, holes, or slots that cooperate with each other.

According to one aspect of the present invention, one of the first electrical contacts or the second electrical contacts is a rigid metal pin or an elastic conductive member.

According to one aspect of the present invention, the type of the elastic conductive member or the elastic conductor includes conductive spring, conductive leaf spring, conductive rubber, or conductive silica gel.

According to one aspect of the present invention, one of the first electrical contacts is a rigid metal pin while one of the second electrical contacts is a conductive spring, a groove, within which a sealing element is provided, is disposed around the area where multiple second electrical contacts are disposed.

According to one aspect of the present invention, the elastic conductor is the conductive leaf spring.

According to one aspect of the present invention, the case includes upper case and lower case.

According to one aspect of the present invention, the type of the power supply includes double-row battery pack.

According to one aspect of the present invention, the power supply include more than one button batteries.

According to one aspect of the present invention, the lower case further includes an outward extending portion, and a block is provided on the outside of the outward extending portion.

According to one aspect of the present invention, the outer end of the outward extending portion is provided with a pressing portion.

Compared with the prior art, the technical solution of the present invention has the following advantages:

In the patch-type drug infusion device disclosed by the present invention, an infusion structure including a case, a power supply, a flexible circuit board, and an elastic conductor. The shape of the flexible circuit board is plastic, allowing it to be flexibly designed according to the internal space of the infusion structure, making the structure more compact and improving the space utilization rate inside the infusion structure. Secondly, one end of the elastic conductor is electrically connected to the electrical connection end on the flexible circuit board while the other end is electrically connected to the power supply. The elastic conductor can help to improve the connection reliability between the power supply and the flexible circuit board. Thirdly, the first electrical contacts are disposed on the control structure while the second electrical contacts on the infusion structure. The contact area of the electrical contact is small, which facilitates the structure design and helps reducing the volume of the control structure.

Furthermore, the type of the elastic conductive member includes conductive spring, conductive leaf spring, conductive rubber, or conductive silica gel. An elastic conductive member, compared with a fixed contact, can further increase the reliability of the electrical connection.

Furthermore, the type of the power supply includes double-row battery pack. The double-row design of the power supply can make full use of the internal space and improve the integration of the internal structure in the infusion device.

Furthermore, the bottom of the case further includes an outward extending portion, and a block is provided on the outside of the outward extending portion. The block can prevent the control structure from detaching from the infusion structure.

DETAILED DESCRIPTION

Figure 1A:
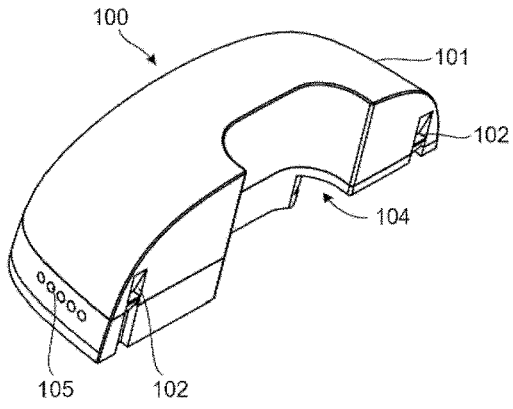
FIG. 1a and FIG. 1b are respectively schematic views of the control structure according to an embodiment of the present invention.

As mentioned above, in the prior art, the internal space utilization rate of the infusion component is low, and the structure is not compact, resulting in larger volume of the infusion device.

Studies have found that the cause of the above-mentioned problem is that PCB is mostly used in existing infusion devices, which have a fixed shape and are not flexible enough.

In order to solve this problem, the present invention provides a drug infusion device which is provided with a flexible circuit board with strong plasticity. According to the structural characteristics, the internal space of the infusion structure can be fully utilized, making the structure more compact and improving the space utilization rate inside the infusion structure.

Various exemplary embodiments of the present invention will now be described in detail with reference to the drawings. The relative arrangement of the components and the steps, numerical expressions and numerical values set forth in the embodiments are not to be construed as limiting the scope of the invention.

In addition, it should be understood that, for ease of description, the dimensions of the various components shown in the figures are not necessarily drawn in the actual scale relationship, for example, the thickness, width, length or distance of certain units may be exaggerated relative to other structures.

The following description of the exemplary embodiments is merely illustrative, and is not intended to be in any way limiting the invention and its application or use. The techniques, methods and devices that are known to those of ordinary skill in the art may not be discussed in detail, but such techniques, methods and devices should be considered as part of the specification.

It should be noted that similar reference numerals and letters indicate similar items in the following figures. Therefore, once an item is defined or illustrated in a drawing, it will not be discussed further in following description of the drawings.

Figure 1B:
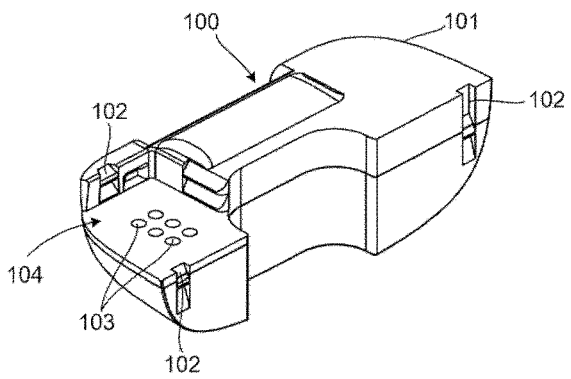

FIG. 1a-FIG. 1b are schematic views of the control structure 100 according to an embodiment of the present invention.

The patch-type drug infusion device of the embodiment of the present invention includes two main parts: a control structure 100 and an infusion structure 110, which will be described separately in detail below. And in another embodiment of the present invention, the patch-type drug infusion device can be provided with more than two parts, which is not specifically limited herein.

The patch-type drug infusion device refers to a tubing-free infusion device that is entirely pasted on the user's skin surface by the one piece of medical tape 120. And the infusion device is provided with an infusion needle unit 121, integrated on the infusion device, instead of a long tube, therefore, drug can be directly infused from the drug reservoir 131 to the subcutaneous tissue through the infusion needle unit 121.

The patch-type drug infusion device of the embodiment of the present invention includes a control structure 100 which receives signals or information from a remote device or a body fluid parameter detection device (such as CGM), and controls the infusion device to infuse drug(s) accordingly.

Inside the housing 101 of the control structure 100 are disposed program modules, circuit board(s) and related electronic units for receiving signals or issuing control instructions, as well as other mechanical units or structures necessary for realizing the infusion function, which is not limited herein. In another embodiment of the present invention, a power supply 133 can be also provided in the control structure. Preferably, in the embodiment of the present invention, the power supply 133 is provided in the infusion structure 110, which will be described below.

The control structure 100 further includes multiple first electrical contacts 103 exposed on the surface of it. The first electrical contact 103 is used as circuit connection terminal for electrically connecting the internal circuits provided in the control structure 100 and the infusion structure 110, respectively. The embodiment of the present invention does not specifically limit the positions of first electrical contacts 103.

Compared with the plug connector used as connection terminal in the prior arts, the contact area of the electrical contact is much smaller, which provides more flexibility to the structure design, and can effectively reduce the volume of the control structure. At the same time, these smaller electrical contacts can be directly electrically connected to the internal circuit or electrical components, or can be directly soldered on the circuit board, which helps to optimize the design of the internal circuit and effectively reduce the complexity of the circuit, thereby, saving costs and reducing the volume of the infusion device. Furthermore, the electrical contacts are exposed on the surface of the control structure 100 to facilitate electrical connection with connection ends on other structures. The above technical advantages of the electrical contacts are applicable to both the first electrical contact 103 on the control structure 100 and the second electrical contact 113 on the infusion structure 110, which will not be described respectively in detail below.

The type of the first electrical contact 103 includes rigid metal pins or elastic conductive members. Preferably, in the embodiment of the present invention, the first electrical contact 103 is a rigid metal pin. One end of the first electrical contact 103 is electrically connected to the connection end provided inside the control structure 100 while the other end is exposed on the surface of the housing 101. And the rest part of the first electrical contact 103 is tightly embedded in the housing 101, thus keeping the inside of the control structure 100 isolated from the outside.

Here, the type of the elastic conductive member includes conductive spring, conductive silica gel, conductive rubber, or conductive leaf spring. Obviously, one end of the elastic conductive member is used to electrically connect with the internal connection end in the control structure 100 while the other end is used to electrically connect with other connection ends. As in an embodiment of the present invention, the first electrical contact 103 is a conductive spring. When the electrical contacts are in contact with each other, the elasticity of the conductive spring can enhance the reliability of the electrical connection. Similar to the rigid metal pin, one end of the conductive spring is exposed on the surface of the housing 101, while the rest part of the conductive spring is tightly embedded in the housing 101 and electrically connected with internal circuits or electrical components. Obviously, the connection end disposed inside the control structure 100 can be a conductive lead, a specific part of a circuit, or an electrical element.

It should be noted that the "tightly embedded" in the embodiment of the present invention means that there is no gap between the electrical contact and the housing 101, keeping the control structure 100 tightly sealed. The following "tightly embedded" has the same meaning as here.

In another embodiment of the present invention, the first electrical contact 103 is a conductive spring, but it is not tightly embedded in the housing 101. Instead, a sealing element is provided in a groove, both of which are disposed around the area where the first electrical contacts 103 are located, thus, sealing the electrical contact area and the control structure 100.

In the embodiment of the present invention, the control structure 100 is further provided with first fastening portions 102 which is used to fasten with the second fastening portion 112 disposed on the infusion structure 110 to assemble the control structure 100 and the infusion structure 110, thereby enabling the electrical connection between the first electrical contacts 103 and the second electrical contacts 113, which will be described in detail below.

The first fastening portion 102 and the second fastening portion 112 include one or more of hooks, blocks, holes, and slots that can be fastened with each other. The positions of the hooks, blocks, holes, and slots can be flexibly adjusted according to the shape and structure features of the control structure 100 and the infusion structure 110, such as disposed in the interior or on the surface of the corresponding structure, which is not specifically limited herein.

In the embodiment of the present invention, the control structure 100 is further provided with a concave 104 that fits the convex portion 114 disposed at the bottom of the case of the infusion structure 110, which will be described in detail below. Preferably, the first electrical contacts 103 are provided in the concave 104, as shown in FIG. 1B.

In the embodiment of the present invention, a buzzer (not shown) is also provided in the control structure 100. When the infusion process starts or ends, the infusion device malfunctions, the drug is exhausted, the control structure 100 issues an error command or receives an error message, etc., the buzzer is used to issue alarm signals, such as sound or vibration, notifying the user to adjust or replace the device in time.

Preferably, in the embodiment of the present invention, the housing 101 of the control structure 100 is provided with a sound-permeable outlet 105 to allow the sound alarm signal from the buzzer to be sent out. In order to achieve a good sealing effect and ensure the normal operation of the buzzer, a waterproof sound-permeable membrane (not shown) is disposed between the sound-permeable outlet 105 and the buzzer. Therefore, the waterproof sound-permeable membrane needs to have a certain porosity to ensure the sound transmission but prevent water molecules penetration.

Compared with the traditional technical solution in which the buzzer is entirely enclosed in the control structure 100, because of the sound-permeable outlet 105, a less loud sound signal emitted from the buzzer would be enough to raise the user's attention, which reduces the energy consumption of the buzzer, thereby optimizing the power consumption configuration of the infusion device and saving production costs.

Figure 2A:
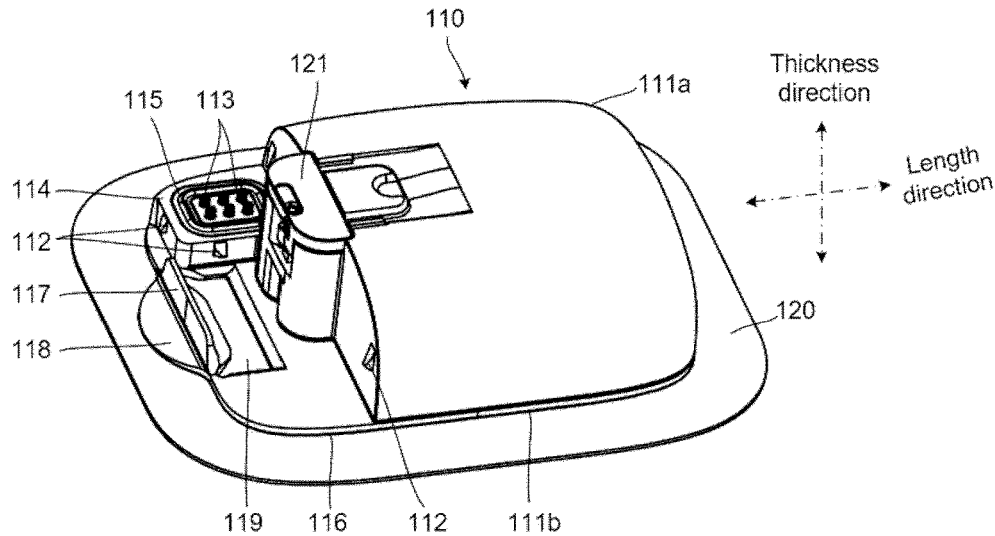
FIG. 2a is a schematic view of the infusion structure according to an embodiment of the present invention.
Figure 2B:
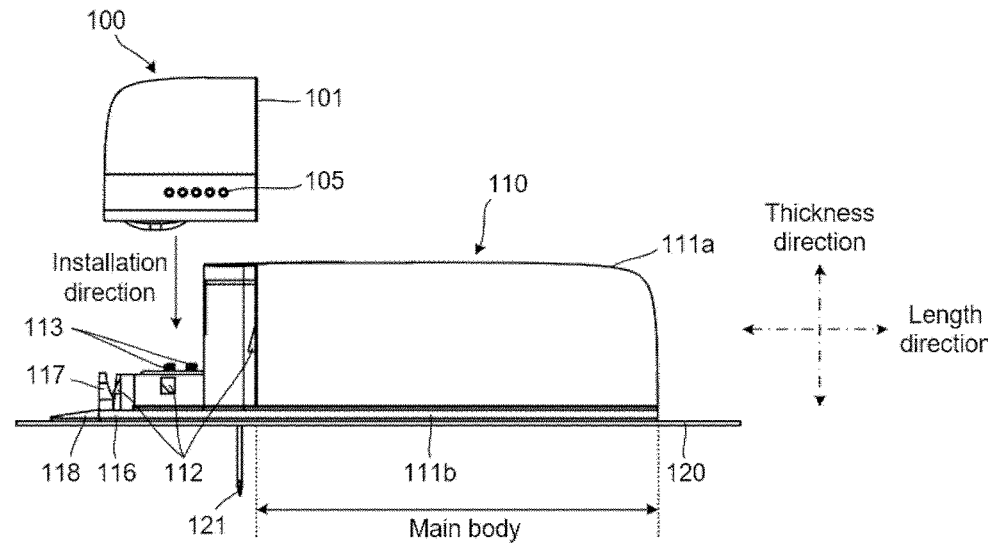
FIG. 2b is a side view of the assembly of the control structure and the infusion structure according to an embodiment of the present invention.
Figure 2C:
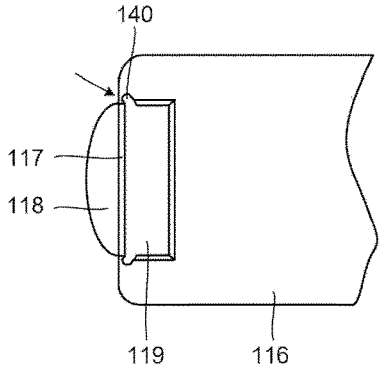
FIG. 2c is a schematic top view of the lower case of the infusion structure according to an embodiment of the present invention.
Figure 2D:
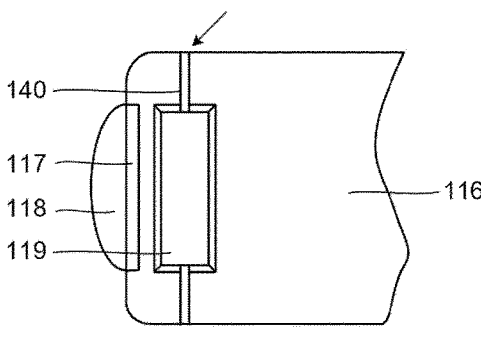
FIG. 2d is a schematic top view of the lower case of the infusion structure according to another embodiment of the present invention.

FIG. 2a is a schematic view of the infusion structure 110 according to the embodiment of the present invention. FIG. 2b is a side view of the assembly of the control structure 100 and the infusion structure 110 according to the embodiment of the present invention. FIG. 2c is a schematic top view of the lower case of the infusion structure according to an embodiment of the present invention. FIG. 2d is a schematic top view of the lower case of the infusion structure according to another embodiment of the present invention.

The patch-type drug infusion device further includes an infusion structure 110 with a case. A mechanical unit, an electric control unit, and other auxiliary units for completing drug infusion process are provided inside the case, which will be described in detail below. The case of the infusion structure 110 may include multiple parts. As in the embodiment of the present invention, the case of the infusion device includes an upper case 111a and a lower case 111b.

As mentioned above, in the embodiment of the present invention, the infusion structure 110 is provided with the second fastening portions 112 which is used to cooperate and fasten with the corresponding first fastening portions 102. Therefore, the positions where the first fastening portion 102 and the second fastening portion 112 are provided correspond to each other.

In the embodiment of the present invention, the infusion structure 110 is provided with second electrical contacts 113 which are used to press against the corresponding first electrical contacts 103 to create electrical connection between the control structure 100 and the infusion structure 110. The mutual pressing between these two corresponding electrical contacts disposed on different structures can improve the reliability of the electrical connection. Similar to first electrical contacts 103, the type of one of the second electrical contact 113 also includes a rigid metal pin and an elastic conductive member. Preferably, in the embodiment of the present invention, the second electrical contact 113 is a conductive spring. Similarly, the conductive spring can improve the electrical connection performance. A groove is also arranged around the area where the second electrical contact 113 is disposed, and a sealing member 115 is arranged in the groove. Similarly, the elasticity of the conductive spring can further improve the electrical connection performance.

Preferably, in the embodiment of the present invention, the two ends of the conductive spring have different diameters. And the diameter of the end exposed to the outside of the infusion structure 110 is shorter than that of the end inside the infusion structure 110. In this way, the conductive spring can be held in the case because of the longer diameter, thus, when the control structure 100 is not installed on the infusion structure 110, the longer diameter of the inner end can prevent the conductive spring from detaching from the infusion structure 110.

The embodiment of the present invention does not limit the position where second electrical contacts 113 are arranged, as long as it can be electrically connected to the corresponding first electrical contacts 103. Preferably, in the embodiment of the present invention, the upper case 111a of the infusion structure 110 includes a convex portion 114 where the second electrical contacts 113 are disposed, as shown in FIG. 2a. The shape of the convex portion 114 corresponds to that of the concave 104 disposed on the control structure 100, allowing the two portions to tightly fit each other and press the first electrical contacts 103 and the corresponding second electrical contacts 113 against each other to realize electrical connection.

In other embodiments of the present invention, the convex portion 114 may be provided on the lower case 111b, or when the infusion structure 110 includes a integral case, the convex portion 114 is a part of the integral case, which is not specifically limited herein.

The method of assembling the control structure 100 and the infusion structure 110 to each other includes pressing the control structure 100 on the infusion structure 110 along with the thickness direction of the infusion structure 110, thereby fastening the first fastening portion 102 and the second fastening portion 112. Or pressing the control structure 100 on the infusion structure 110 along with the length direction of the infusion structure 110. Or alternatively, the control structure 100 can be pressed along with any angle between the thickness direction and the length direction of the infusion structure 110, making the first fastening portion 102 and the second fastening portion 112 fastened with each other. Preferably, in the implementation of the present invention, the method of which the control structure 100 and the infusion structure 110 are assembled with each other is to press the control structure 100 on the infusion structure 110 along with the thickness direction of the infusion structure 110, making the first fastening portion 102 and the second fastening portion 112 fastened with each other, as shown the installation direction in FIG. 2b.

In the embodiment of the present invention, the lower case 111b of the infusion structure 110 further includes an outward extending portion 116, and a block 117 is provided on the outside of the outward extending portion 116, as shown in FIG. 2a. As mentioned above, the control structure 100 is pressed to the fastening position along the thickness direction of the infusion structure 110, thus the block 117 can prevent the control structure 100 from detaching along the length direction of the infusion structure 110, ensuring the normal operation of the infusion device. Obviously, in another embodiment of the present invention, if the control structure 100 is pressed to the fastening position along with other directions, the control structure 100 can also be prevented from detaching from the infusion structure 110 by adjusting the position of the block 117.

It should be noted here that "outward" and "outside" are relative to the main body of the infusion structure 110, and belong to a concept of relative position, whose position relationship is shown in FIG. 2a or FIG. 2b. The "outside" below has the same meaning as here.

In the embodiment of the present invention, the outer end of the outward extending portion 116 is also provided with a pressing portion 118 for releasing the blocking effect of the block 117. While the user is replacing the infusion structure 110, a finger presses the pressing portion 118, releasing the control structure 100 from the block 117. Then, the user can remove the control structure 100 from the infusion structure 110 with another two fingers.

Another embodiment of the present invention can also be provided with an unlocking hole 119 disposed in the inner side of the block 117. While the pressing portion 118 is being pressed, a finger can enter the unlocking hole 119, thereby pushing the control structure 100 out to separate the control structure 100 from the infusion structure 110. In the embodiment of the present invention, the unlocking hole 119 is square. The square unlocking hole 119 can facilitate smooth entry of fingers. In other embodiments of the present invention, the unlocking hole 119 may also have other shapes, which is not specifically limited here.

The lower case 111b of the infusion structure 110 is also provided with one or more crease grooves 140. Two crease grooves 140 are provided on both sides of the unlocking hole 119, as shown in FIG. 2c and FIG. 2d. After the crease groove 140 is provided, the thickness or width of the lower case 111b at the position of the crease groove 140 (as shown by the arrows in FIG. 2c and FIG. 2d) is reduced. When the user presses the pressing portion 118, the lower case 111b is easy to be broken at the position of the crease groove 140, and the blocking of the control structure 100 by the block 117 is more smoothly released.

Preferably, in the embodiment of the present invention, two crease grooves 140 are provided at the two ends of the block 117 respectively, as shown in FIG. 2c. In another embodiment of the present invention, the crease groove 140 is provided on two corresponding lateral sides of the unlocking hole 119, as shown in FIG. 2d.

The infusion structure 110 of the embodiment of the present invention is further provided with an infusion needle unit 121 for infusing the drug under the skin.

A medical tape 120 is also provided on the bottom of the lower case 111b for attaching the infusion device on the surface of the user's skin.

Figure 3A:
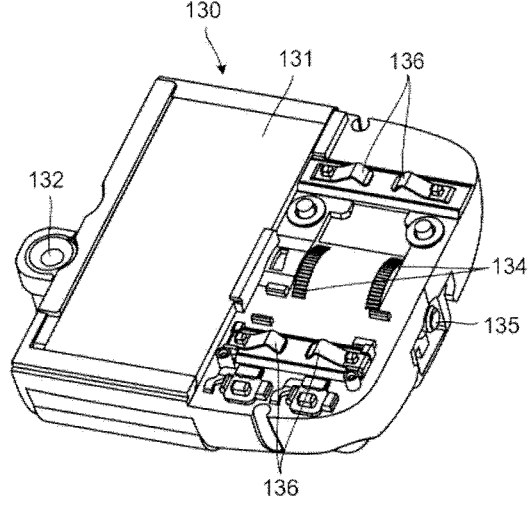
FIG. 3a and FIG. 3b are respectively schematic views of the internal structure of the infusion structure according to an embodiment of the present invention.
Figure 3B:
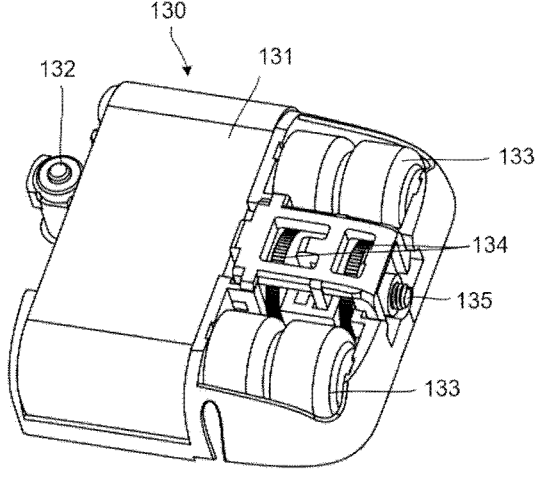

FIG. 3a and FIG. 3b are respectively two schematic views of the internal structure 130 of the infusion structure 110 of the embodiment of the present invention from two perspectives.

In the embodiment of the present invention, the internal structure 130 includes mechanical units and electronic control units, used to realize the infusion function, such as a drug reservoir 131, a drug outlet 132, a power supply 133, a driving wheel 134, a screw 135, a circuit board (not shown), a driving unit (not shown), etc. The movement of the driving unit drives the driving wheel 134 to rotate, thus making the screw 135 push the piston (not shown) in the drug reservoir 131 to forward, realizing the drug infusion.

In the embodiment of the present invention, the power supply 133 is a conventional button battery. In other embodiments of the present invention, the power supply 133 may also be other types of batteries, as long as it can meet the requirements for supplying power to the infusion device. Preferably, in the embodiment of this present invention, the type of the power supply 133 is double-row battery pack, that is, two rows of button batteries are respectively arranged on both sides of the driving wheel 134, as shown in FIG. 3b. Conventionally, the discharge capacity of button batteries is low. The double-row button battery pack can reduce the discharge level of each battery, thereby extending the service life of the battery. Furthermore, the double-row design of the power supply 133 can make full use of the internal space and improve the integration of the internal structure in the infusion device.

The infusion structure 110 in the embodiment of the present invention is also provided with a circuit board or a three-dimensional circuit coated on the surface of a part of the structure for supplying power to specific structural units. The circuit board is a hard/rigid circuit board or a flexible circuit board. Preferably, in the embodiment of the present invention, the circuit board is a flexible circuit board. The shape of the flexible circuit board is plastic, allowing it to be flexibly designed according to the internal space of the infusion structure 110. At the same time, multiple connection ends can be provided on the flexible circuit board to be electrically connected to second electrical contacts 113, thereby connecting the circuits of the control structure 100 and the infusion structure 110, letting the infusion device to perform drug infusion function.

An elastic conductor 136 is also provided inside the infusion structure 130, as shown in FIG. 3*a*. The elastic conductor 136 is electrically connected to the power supply 133 and the specific connection end on the circuit board (or three-dimensional circuit), thereby supplying power to specific structural units.

Similar to the elastic conductive member above mentioned, the type of the elastic conductor 136 includes conductive spring, conductive leaf spring, conductive rubber, conductive silica gel, etc., which are not specifically limited herein, as long as they can meet the requirements for electrically connecting the power supply 133 to specific connection ends on the circuit board (or three-dimensional circuit). Preferably, in the embodiment of the present invention, the elastic conductor 136 is the conductive leaf spring. Obviously, since the infusion structure 110 has a double-row battery pack, the multiple conductive leaf springs are also designed as a double-row pack, as shown in FIG. 3*a*.

The elastic conductor 136 can realize direct electrical connection between the power supply 133 and the specific structural units, which helps to optimize the internal circuit design and reduce the complexity of the internal structure.

In summary, the present invention discloses a patch-type drug infusion device which is provided with a flexible circuit board with strong plasticity. According to the structural characteristics, the internal space of the infusion structure can be fully utilized, making the structure more compact and improving the space utilization rate inside the infusion structure.

While the invention has been described in detail with reference to the specific embodiments of the present invention, it should be understood that it will be appreciated by those skilled in the art that the above embodiments may be modified without departing from the scope and spirit of the invention. The scope of the invention is defined by the appended claims.

The invention claimed is:

1. A patch-type drug infusion device, comprising:
a control structure provided with multiple first fastening portions and first electrical contacts exposed on a surface of the control structure; and
an infusion structure including a case, a power supply, a flexible circuit board, and an elastic conductor, wherein one end of the elastic conductor is electrically connected to an electrical connection end on the flexible circuit board while an other end of the elastic conductor is electrically connected to the power supply, the infusion structure is provided with multiple second electrical contacts exposed on a surface of the case and second fastening portions that cooperate with the first fastening portions, the first fastening portions and the second fastening portions are fastened, the first electrical contacts connect with the corresponding second electrical contacts, wherein the case includes an outward extending portion where is configured for the control structure to be assembled, and a block is provided on the outward extending portion, when the control structure is assembled onto the outward extending portion along a first direction, the block is adjacent to the control structure to prevent the control structure from detaching the infusion structure along a second direction.

2. The patch-type drug infusion device of claim 1, wherein
the first fastening portions and the second fastening portions include hooks, blocks, holes, or slots that cooperate with each other.

3. The patch-type drug infusion device of claim 1, wherein
one of the first electrical contacts or one of the second electrical contacts is a rigid metal pin or an elastic conductive member.

4. The patch-type drug infusion device of claim 3, wherein
the elastic conductive member includes a conductive spring, a conductive leaf spring, a conductive rubber, or a conductive silica gel.

5. The patch-type drug infusion device of claim 4, wherein
one of the first electrical contacts is a rigid metal pin while one of the second electrical contacts is a conductive spring, a groove, within which a sealing element is provided, is disposed around an area where the second electrical contacts are disposed.

6. The patch-type drug infusion device of claim 4, wherein
the elastic conductor is the conductive leaf spring.

7. The patch-type drug infusion device of claim 1, wherein
the case includes an upper case and a lower case.

8. The patch-type drug infusion device of claim 1, wherein
the power supply includes a double-row battery pack.

9. The patch-type drug infusion device of claim 1, wherein
the power supply includes button batteries.

10. The patch-type drug infusion device of claim 1, wherein
an outer end of the outward extending portion is provided with a pressing portion.

* * * * *